US008806946B2

(12) United States Patent
Flister et al.

(10) Patent No.: US 8,806,946 B2
(45) Date of Patent: Aug. 19, 2014

(54) SYSTEM AND METHOD FOR DETECTING DEPOSITS IN A FLUID LINE

(75) Inventors: Michael Flister, Neu Wulmstorf (DE); Wilhelm Lutzer, Zarpen (DE)

(73) Assignee: Airbus Operations GmbH, Hamburg (DE)

( * ) Notice: Subject to any disclaimer, the term of this patent is extended or adjusted under 35 U.S.C. 154(b) by 340 days.

(21) Appl. No.: 13/416,097

(22) Filed: Mar. 9, 2012

(65) Prior Publication Data

US 2012/0222484 A1 Sep. 6, 2012

Related U.S. Application Data

(63) Continuation of application No. PCT/EP2010/063111, filed on Sep. 7, 2010.

(60) Provisional application No. 61/241,278, filed on Sep. 10, 2009.

(30) Foreign Application Priority Data

Sep. 10, 2009 (DE) .......................... 10 2009 040 999

(51) Int. Cl.
G01N 29/04 (2006.01)
(52) U.S. Cl.
USPC ................................................ 73/623; 73/602
(58) Field of Classification Search
USPC .............. 73/623, 152.57, 597, 598, 602, 622, 73/628, 703
See application file for complete search history.

(56) References Cited

U.S. PATENT DOCUMENTS

| 4,450,711 | A | * | 5/1984 | Claude ........................ 73/40.5 R |
| 4,669,310 | A | | 6/1987 | Lester |
| 4,735,047 | A | * | 4/1988 | Wiedmann ...................... 60/415 |
| 6,474,165 | B1 | | 11/2002 | Harper et al. |
| 6,615,848 | B2 | | 9/2003 | Coats |
| 7,095,676 | B2 | * | 8/2006 | D'Angelo et al. ............... 367/31 |
| 7,369,948 | B1 | * | 5/2008 | Ferenczi et al. ................ 702/35 |
| 8,181,535 | B2 | * | 5/2012 | Huang et al. ................ 73/861.25 |

FOREIGN PATENT DOCUMENTS

| DE | 10214678 A1 | 10/2003 |
| DE | 102007004278 A1 | 7/2008 |
| JP | 60196662 A | 10/1985 |

OTHER PUBLICATIONS

German Patent Office, German Office Action dated Mar. 24, 2010 for German Patent Application No. 10 2009 040 999.8.
International Searching Authority, International Search Report for International Application No. PCT/EP2010/063111 dated Sep. 26, 2011.

* cited by examiner

Primary Examiner — J M Saint Surin
(74) Attorney, Agent, or Firm — Ingrassia Fisher & Lorenz P.C.

(57) ABSTRACT

A system is provided for the detection of deposits in a fluid line that includes, but is not limited to a measuring body, and ultrasonic transducer and an ultrasonic receiver and at least one evaluation unit connected to the ultrasonic transducer and the ultrasonic receiver. The ultrasonic transducer transmits an ultrasonic signal and the ultrasonic receiver receives response signals generated by reflections in the fluid line. From known geometric changes in shape of the fluid line, resulting response signals are finally filtered out of the response signal sequence and from the remaining response signals relating to the deposits, the distances can be calculated between the ultrasonic transducer and the deposits.

18 Claims, 4 Drawing Sheets

SYSTEM AND METHOD FOR DETECTING DEPOSITS IN A FLUID LINE

CROSS-REFERENCE TO RELATED APPLICATIONS

This application is a continuation of International Application No. PCT/EP2010/063111, filed Sep. 7, 2010, which claims priority to U.S. Provisional Patent Application No. 61/241,278, filed Sep. 10, 2009, and also claims priority to German Patent Application No. 10 2009 040 999.8, filed Sep. 10, 2009, the contents of which applications are incorporated herein by reference.

TECHNICAL FIELD

The technical field relates to a system and a method for detecting deposits in a fluid line.

BACKGROUND

Deposits and blockages in fluid lines are often detected when a regular flow volume of the fluid through the line in question is no longer attained. When this occurs, it is clear that there are either deposits or blockages. In order to remove these deposits, especially in the case of lengthy fluid lines or complex fluid line systems, it is advantageous to be able to determine the precise location of these deposits, so that appropriate action can be taken by mechanical means. By successively disassembling parts of the fluid line, it is possible to determine the precise location. Alternatively, it is possible to identify and to remove deposits in the fluid line in question by inserting extended pipe cleaning devices into the line in question.

However, in the case of complex fluid line systems, or where there are numerous changes in the direction or the cross-section of the line, or in cases where there are particularly solid ad hoc blockages, this cannot always be resolved within a short space of time. For example, large vehicles carrying a high volume of passengers, such as a commercial aircraft, can contain many fluid lines that can be subject to blockages. This refers to all types of fluid lines, in particular, drainage lines from toilets and washbasins. Because of the complexity and the length of the fluid lines and the fluid conduction systems in a vehicle and also the high number of additional on-board components installed in the vicinity of these fluid lines, it is not possible to trace deposits and blockages in such fluid lines by successively disassembling parts of the fluid line system, without taking the vehicle out of service for a longer period, which would not be economically viable. Any preventive clearing or cleaning of fluid lines in the manner recommended in the maintenance handbooks of commercial aircraft at rigidly prescribed intervals using chemicals that may not be universally recognised as being safe will incur additional costs in the purchase of the chemicals in question and could even be the cause of corroding the fluid lines themselves as well as the seals in and around the fluid line.

Accordingly, at least one object may be regarded as proposing a system for the detection of deposits in a fluid line, in which the successive disassembling of the fluid line in order to establish the location of deposits is not necessary. At least a further object may be to control intervals of preventive maintenance of fluid lines by means of chemicals and when necessary, that is to say, once deposits have been detected. In addition, other objects, desirable features, and characteristics will become apparent from the subsequent summary and detailed description, and the appended claims, taken in conjunction with the accompanying drawings and this background.

According to a first embodiment, a system comprises a measuring body with an ultrasonic transducer and an ultrasonic receiver and at least one evaluation unit that is connected to the ultrasonic transducer and the ultrasonic receiver. The ultrasonic transducer and the ultrasonic receiver are arranged on the measuring body. The evaluation unit is adapted for storing data of changes in the direction and the cross-section of a fluid line. At the same time, it is capable of determining periods of time between ultrasonic signals that are sent out and the signals that are received in response and of filtering the response signals that relate exclusively to the stored data of changes in cross-sections and directions of the fluid line. Lastly, from the remaining signals relating to deposits, the evaluation unit is adapted for calculating the distances between the free end of the ultrasonic transducer and the deposits.

In other words, ultrasonic signals are sent from the measuring unit into the fluid line and the resulting response signals are received. It is particularly advantageous if the ultrasonic signals can be inserted directly into the fluid line in a line axial direction, so that they essentially travel in the directional axis of the fluid line. The response signals captured by the ultrasonic receiver arise at every change of direction or bend in the line, at significantly effective changes in the cross-section of the fluid line and when deposits in the fluid line are encountered. Depending upon the severity of the case, a correspondingly strong reflected signal, hereinafter referred to as a "response signal," is returned via the fluid line and finally captured by the ultrasonic receiver. In the event of a number of changes of geometrical shape and/or deposits being captured, the ultrasonic receiver receives a quantity of response signals, referred to below as "sequence of response signals." The period of time between the ultrasonic signal emission and a point in time of the reflection, that is to say of the generation of a respective response signal, corresponds to the distance between the position of the ultrasonic transducer and the place at which the reflection in question occurs.

For determining the response signals that emanate exclusively from deposits, the evaluation unit is adapted for storing all data for the fluid line in question relating to all possible geometric changes of shape encountered in the fluid line in an installed state. All these geometric changes in shape can be matched to a characteristic response signal that has a characteristic duration and a characteristic amplitude. The evaluation unit is adapted for filtering out from this data set all characteristic response signals from the sequence of response signals by means of a pattern recognition or a system of difference recognition. This also means that in the response signal sequence only remain response signals that relate to deposits or blockages and not those relating to any geometric changes in form of the fluid line. From the knowledge of the periods of time elapsing between the sending of the ultrasonic signal and the capture of the remaining response signals, the location of each deposit within the fluid line can be determined. Finally, by evaluating the respective amplitude pattern of the remaining response signals, it will be possible to calculate the size and the layer thickness of the different deposits.

In another embodiment of the system, the evaluation unit is adapted for carrying out a self-calibration on the basis of the stored data. In this way, if the ultrasonic transducer and the ultrasonic receiver are not accurately positioned when the measuring body is put into position, no precise information can be obtained as to the precise location of the deposits, as the locations established depend on the relative position of the ultrasonic transducer and the ultrasonic receiver in the fluid line. On the basis of a determined response signal sequence, which is compared with the stored data containing geometric changes in the fluid line, the precise relative positions of the ultrasonic transducer and the ultrasonic receiver can be established in relation to the fluid line. These determined relative positions can be used to calibrate the evaluation unit or an algorithm executed in the latter in order to identify deposits, in that the relative positions are taken into account in the subsequent detection or already in the received response signal sequence of deposits.

It is especially preferred that the measuring body is made of an elastic material and comprises an elongated form. This allows the measuring body to be inserted into an open end of a fluid line, such as a toilet bowl, a wash basin or the like. The measuring body may be realized as a flexible hose section.

In another embodiment of the system, the evaluation unit is adapted for determining the tangential slope of response signals, i.e., the development of the amplitude over time and the envelope curve of the response signal, respectively or another significant feature and for detecting the extent of the deposits that through the determined tangential slopes.

In another embodiment of the system, the evaluation unit is adapted for generating display data for a spatially resolved representation of deposits in the fluid line. In this way, the distances from the ultrasonic transducer and the ultrasonic receiver to the deposit can both be given and marked on a graduated sale for the fluid line in question. This means that a display can be created, on which an operator can clearly see where the deposit that needs to be removed is located in the fluid line.

A further embodiment of the system is realized as a mobile, portable unit.

The ultrasonic transducer and the ultrasonic receiver can be particularly advantageously constructed as so-called ultrasonic transceivers, which, in the form of a single compact structural unit, can perform the function of emitting the ultrasonic signal and also that of receiving the response signals.

A method is also provided according to an embodiment, and a use of a system according to an embodiment in a fluid line of an aircraft.

BRIEF DESCRIPTION OF THE DRAWINGS

The present invention will hereinafter be described in conjunction with the following drawing figures, wherein like numerals denote like elements, and.

DETAILED DESCRIPTION

The following detailed description is merely exemplary in nature and is not intended to limit application and uses. Furthermore, there is no intention to be bound by any theory presented in the preceding background or summary or the following summary and detailed description.

Figure 1:
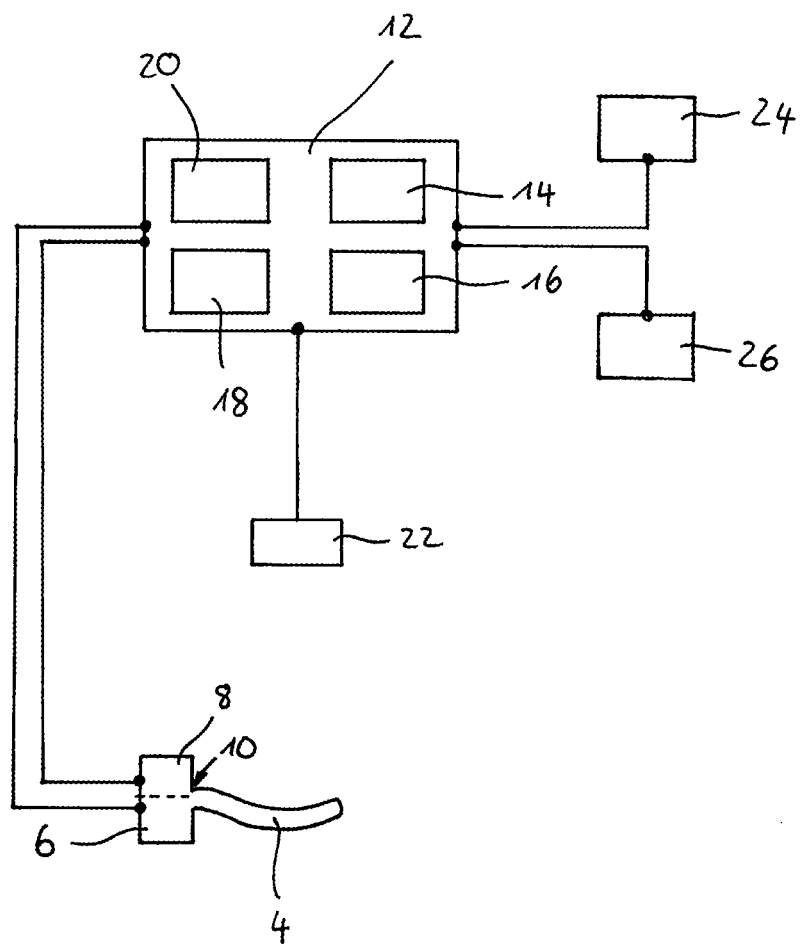
FIG. 1 shows a schematic view of the system according to an embodiment.

Schematically, FIG. 1 shows a system 2 according to an embodiment, comprising a measuring body 4, which is connected to an ultrasonic transducer 6 and an ultrasonic receiver 8. The ultrasonic transducer 6 and the ultrasonic receiver 8 can also be realized in the form of a so-called "ultrasonic transceiver," in which ultrasonic signals can be both sent and received by a single component.

The ultrasonic transducer 6 and the ultrasonic receiver 8 are arranged at one end 10 of the measuring body 4. The measuring body 4 has an elongated shape and preferably has a hose like shape which permits the passage of ultrasonic waves. Because of its shape, the measuring body 4 is easily insertable into a fluid line that requires testing without any partial disassembly of the fluid line being necessary. The use of an elastic material means that the measuring body 4 can bear even quite considerable changes in the shape of the fluid line, which can be found for example in openings into wash basins or toilet bowls, into which the measuring body 4 can be introduced. The ultrasonic transducer 6 and the ultrasonic receiver 8 are connected to an evaluation unit 12, which can cause the ultrasonic transducer 6 to send ultrasonic waves into the fluid line. Similarly, the response signal sequences received by the ultrasonic receiver 8 can be relayed to the evaluation unit 12, where they can be further processed.

The evaluation unit 12 comprises a central data processing unit 14, in which the evaluation of the response signal sequences in the form of pattern recognitions, difference considerations or correlation can be carried out with the aid of suitable algorithms. The evaluation unit 12 is connected to a memory unit 16, which contains all data relating to all relevant geometric changes of shape of the fluid line in question, including in particular changes in the direction and in the cross-section of the fluid line. The evaluation unit 12 is therefore capable of filtering out any response signals contained in the response signal sequences that relate to known geometric changes in shape in the fluid line that are determined by installation factors. For evaluation purposes a reference signal sequence could be generated in the form of a simulation of a received response signal sequence of a "clean" fluid line free of any deposits. By subtracting this reference signal sequence from the response signal sequence actually received by the ultrasonic receiver 8 a "cleaned" response signal sequence may be obtained, in which the response signals resulting from the geometric changes in shape of the fluid line are no longer present and the signals represent exclusively undesirable deposits. From these calculated response signals, and on the basis of the diffusion speed of the ultrasonic waves in the fluid line, it is possible to calculate the distance to all incidents that can trigger the response signals, which correspond to the distance to the respective deposit.

Furthermore, the evaluation unit 12 is adapted for calculating the tangential slope and the envelope curve, respectively or any other significant feature of the response signal. In this respect, it should be noted that the amount of extension of the deposit in the longitudinal direction of the fluid line is in inverse proportion to the tangential slope. At the same time, the evaluation unit 12 can also comprise a display unit 18, which is adapted to show the display data relating to the deposits that have been determined. Knowing the geometric shape of the fluid line and the distance to the deposit in question, it is possible to show in a spatially resolved manner the location of the deposit within the fluid line. This could be achieved for example by showing a graphic representation of the fluid line, in which the detected deposits are shown in the form of markings. Furthermore, the evaluation unit 12 can comprise a reading device 20, into which a memory card, a diskette or any other memory medium can be inserted and read back in order to provide the memory unit 16 with up to date data of the respective fluid line.

Finally, the system can also comprise a data transmission system 22, which is connected to the evaluation unit 12. The evaluation unit 12 can therefore be adapted for communicating with the external maintenance system of a vehicle. This is particularly relevant for use in commercial aircraft, which are regularly maintained and for which a maintenance system containing information on all relevant vehicle data could be provided. In this way, even without an external memory medium, the evaluation unit 12 could receive stored data on the geometric changes in shape of the respective fluid line and at the same time communicate information on the detected deposits to the maintenance system via the data transmission system 22, so that an technician could be shown from which points of the respective fluid lines deposits or blockages needed to be removed. The data transmission unit is preferably a wireless data transmission unit, so as to ensure the mobility of the system according to the invention.

Finally, the system 2 can also comprise a display 24 and control elements 26, by means of which a user can choose which of the possible fluid lines in an aircraft or the like is to be tested for deposits. For the purpose of simplification, an appropriate device in the fluid line, for example a wash basin or a toilet bowl, could be marked at a hidden spot with a bar code or an RFID tag, with which the system could be easily detected as necessary by a suitable scanner (not shown in FIG. 1) to determine which fluid line is currently being examined, so that the relevant data can be loaded or called up. At the same time, by means of the display 24, an acknowledgement from the system 2 can be sent to the user, if an operating error has occurred as a result of a blockage or an incorrect positioning of the measuring body 4 or the like.

Figure 2:
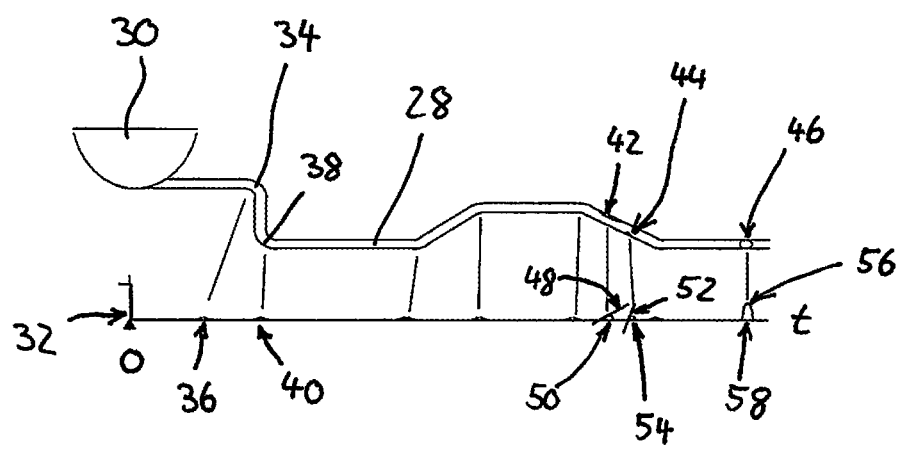
FIG. 2 shows a diagrammatic confrontation of a fluid line with deposits and resulting response signals over time.

FIG. 2 shows a fluid line 28 that is connected to a wash basin 30. This type of washbasin and fluid line 28 could be accommodated in a modern commercial aircraft, in which it is very difficult to detect deposits and blockages in a fluid line, which would need to be successively disassembled in order to verify the cross-section. Below the fluid line 28, a response signal sequence scaled along its length is shown in relation to time following a transmitted ultrasonic signal 32 of currently "0" from reflections within the fluid line 28.

In order to detect deposits, the measuring body 4 is introduced into the fluid line via the wash basin 30. There, for example, the output signal is sent axially in relation to the fluid line 28. Once the initial signal 32 has passed into the fluid line 28 and encountered a first bend 34, it is reflected and reverts to the measuring body 4. This will give rise to a first response signal 36 with a characteristic amplitude and a characteristic tangential slope.

After the non-reflected part of the signal has advanced as far a second bend 38 and is then reflected back to the measuring body 4, a second response signal 40 results, again with a characteristic amplitude and a characteristic tangential slope. The diffusion of the sound waves essentially in an axial direction inside the fluid line 28 has the result that, at all having a geometric change of shape, a characteristic response signal is generated that is caused exclusively by the respective geometric change of shape As the geometric construction of the fluid line 28 is fully known, the resulting response signals can be calculated out of the incoming response signal sequences.

Exemplarily, the fluid line 28 shows two deposits 42 and 44 and a complete blockage 46, through which the wound waves cannot pass. The deposit 42 extends in a longitudinal direction and forms the deposit 44, so that the tangential slope 48 of the third response signal 50 relating to the deposit 42 is flatter than the tangential slope 52 of the fourth response signal 54. The amplitude 56 of a fifth response signal 58 relating to the blockage 46 is significantly greater than the amplitudes of the remaining response signals, which indicates that a complete blockage can be assumed here.

Figure 3:
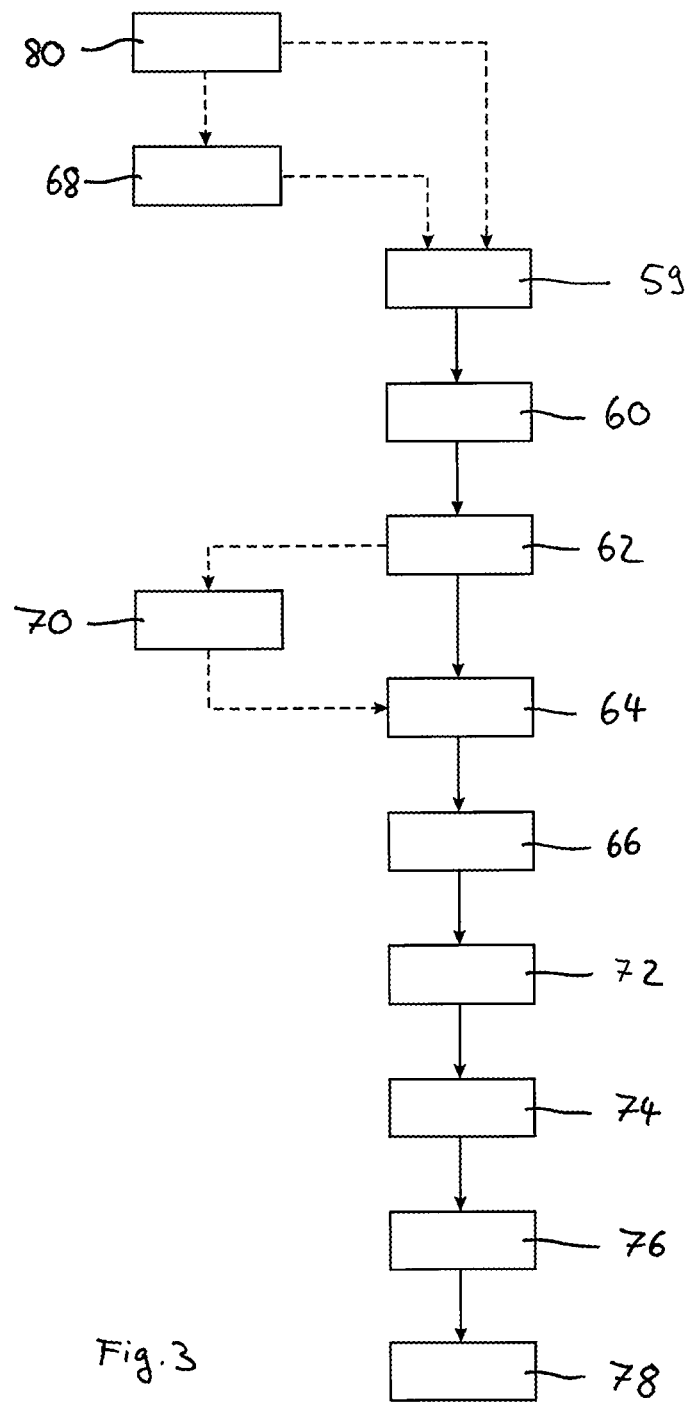
FIG. 3 shows a method according to an embodiment in schematic form.

FIG. 3 contains a schematic representation of the method according to an embodiment in the form of a block diagram. After the transmission 59 of an ultrasonic signal by the ultrasonic transducer 6 into the fluid line 28, resulting response signals from reflections within the fluid line 28 are received 60 by the ultrasonic receiver 8. Finally, response signals from the response signal sequence received that relate to the geometric changes in shape are filtered out 62. The time intervals between the sending out of the ultrasonic signal and the receipt of the response signals is determined 64 and from this, the distances between the ultrasonic transducer 6 and the deposits are calculated 66.

Before conducting the method, a fluid line 28 that has to be examined could be selected 68 by means of a control element 26 and a display 24. At the same time, the method provides for 70 a self-calibration in order to determine the relative position of the ultrasonic transducer to the fluid line. By way of example, without restricting the embodiments, the self-calibration could take place before the filtering out 62 of response signals of geometric changes in form of the fluid line 28.

From the response signals relating to deposits it is also possible for tangential slopes to be determined 72 and from these the size, i.e., the thickness and the extension in the directional axis, of the respective deposits can be calculated 74. Finally, display data can be generated 76 for a spatially resolved representation of deposits that are detected in the fluid line. Optionally, the display data can be transmitted 78 to a maintenance system, through which data relating to geometric changes of shape in the fluid line 28 can also be received 80.

Figure 4:
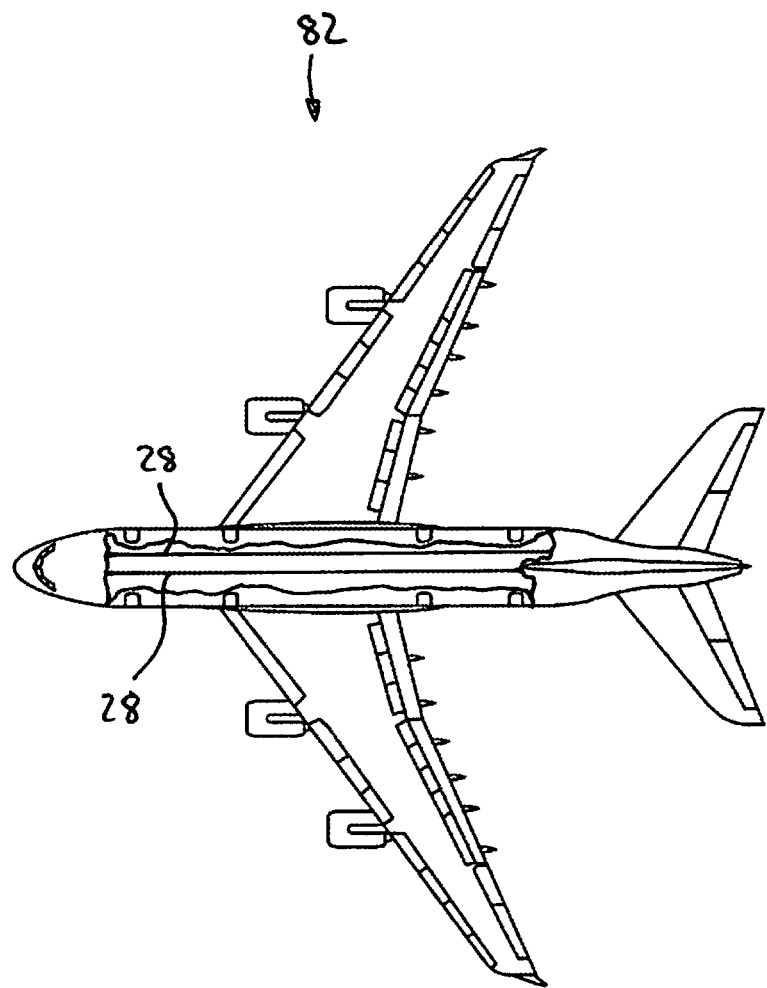
FIG. 4 shows an aircraft with a number of fluid lines, in which the system according to an embodiment can be used in order to implement the method according to an embodiment.

FIG. 4 shows an aircraft 82 fitted with a number of fluid systems 28. The method, which is carried out by the system 2 according to the embodiments, is particularly suited to detecting deposits and blockages in a fluid line 28 in an aircraft, as there is no need for the successive disassembling of parts of the fluid line 28 and the intervals required for keeping the fluid line free of deposits and blockages by the use of chemicals can be controlled as required.

Finally, it must be stressed that the terms "comprising" is not intended to preclude other elements or steps and that "a" or "an" does not preclude a plural form. It is also stressed that features or steps, described by means of references to one of the above embodiments, can also be used in combination with other features or steps of other embodiments described above. Moreover, while at least one exemplary embodiment has been presented in the foregoing summary and detailed description, it should be appreciated that a vast number of variations exist. It should also be appreciated that the exemplary embodiment or exemplary embodiments are only examples, and are not intended to limit the scope, applicability, or configuration in any way. Rather, the foregoing summary and detailed description will provide those skilled in the art with a convenient road map for implementing an exemplary embodiment, it being understood that various changes may be made in the function and arrangement of elements described in an exemplary embodiment without departing from the scope as set forth in the appended claims and their legal equivalents.

What is claimed is:

1. A system for detecting deposits in a fluid line, comprising:
   a measuring body;
   an ultrasound transducer arranged on the measuring body and configured to transmit ultrasonic signals;

an ultrasonic receiver arranged on the measuring body configured to receive a response signal in response to the ultrasonic signals transmitted by the ultrasound transducer; and an evaluation unit connected to the ultrasonic transducer and the ultrasonic receiver;

wherein the measuring body is configured for insertion into an open end of the fluid line also configured to couple in ultrasound signals and send out ultrasonic signals in an axial direction in relation to the fluid line, and wherein the evaluation unit is configured to:

store data relating to geometric changes of a shape of the fluid line;

determine running times between transmitted ultrasonic signals and the response signal received by the ultrasonic receiver from reflections within the fluid line;

filter out the response signal relating to the geometric changes in shape; and calculate distances between the ultrasonic transducer and the deposits from remaining response signals relating to the deposits.

2. The system according to claim 1, wherein the evaluation unit is configured to self-calibrate on at least a basis of the data.

3. The system according to claim 1, wherein the measuring body comprises an elongated shape and comprises an elastic material.

4. The system according to claim 1, wherein the evaluation unit is configured to determine significant features of response signals concerning the deposits and calculate the size of respective deposits from the significant features.

5. The System according to claim 1, wherein the significant features comprise the tangential slopes.

6. The system according to claim 1, further comprising a data transmission unit that is adapted for exchanging data on calculated deposits.

7. The system according to claim 1, further comprising a data transmission unit that is adapted for exchanging data on calculated data on the geometric changes of shape with an external component.

8. The system according to claim 7, wherein the external component is a maintenance system.

9. The method according to claim 7, wherein the external component is a maintenance system.

10. The system according to claim 1, further comprising a display and an operating element to control the evaluation unit.

11. The system according to claim 1, wherein the evaluation unit is configured to generate display data for a spatially resolved representation of detected deposits in the fluid line.

12. A method for detecting deposits in a fluid line, comprising:

transmitting an ultrasonic signal with an ultrasonic transducer into the fluid line;

receiving a response signal resulting from reflections within the fluid line with an ultrasonic receiver;

filtering out response signals relating to stored geometric changes of the shape of the fluid line;

determining running times between the ultrasonic signal and the response signal; and calculating distances between the ultrasonic transducer and from the running times.

13. The method according to claim 12, further comprising selecting the fluid line with a control element at an evaluation unit.

14. The method according to claim 12, further comprising:

self-calibrating in order to determine a relative position of the ultrasonic transducer to the fluid line.

15. The method according to claim 12, further comprising:

determining characteristic features of response signals from the deposits; and calculating the size of respective deposits from the characteristic features.

16. The method according to claim 12, wherein the significant features comprise the tangential slopes.

17. The method according to claim 12, further comprising generating display data for a spatially resolved representation of deposits detected in the fluid line.

18. The method according to claim 12, further comprising exchanging data on calculated data on the geometric changes of shape with an external component.

* * * * *